United States Patent
Tanimura et al.

(10) Patent No.: US 11,028,056 B2
(45) Date of Patent: Jun. 8, 2021

(54) METHOD FOR PRODUCING 3-ARYLPROPIONAMIDE COMPOUND AND 3-ARYLPROPIONIC ACID ESTER COMPOUND

(71) Applicant: SUMITOMO CHEMICAL COMPANY, LIMITED, Tokyo (JP)

(72) Inventors: Shun Tanimura, Takarazuka (JP); Masaya Tanimoto, Anpachi-gun (JP); Koji Hagiya, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/616,596

(22) PCT Filed: May 30, 2018

(86) PCT No.: PCT/JP2018/020798
§ 371 (c)(1),
(2) Date: Nov. 25, 2019

(87) PCT Pub. No.: WO2018/221604
PCT Pub. Date: Dec. 6, 2018

(65) Prior Publication Data
US 2020/0165209 A1    May 28, 2020

(30) Foreign Application Priority Data
May 31, 2017  (JP) .............................. JP2017-107506

(51) Int. Cl.
*C07D 239/42*   (2006.01)
*C07C 67/347*   (2006.01)
*C07C 231/12*   (2006.01)
*C07C 269/00*   (2006.01)
*C07C 69/612*   (2006.01)
*C07C 233/08*   (2006.01)
*C07C 271/14*   (2006.01)

(52) U.S. Cl.
CPC .......... *C07D 239/42* (2013.01); *C07C 67/347* (2013.01); *C07C 231/12* (2013.01); *C07C 269/00* (2013.01); *C07C 69/612* (2013.01); *C07C 233/08* (2013.01); *C07C 271/14* (2013.01)

(58) Field of Classification Search
CPC ... C07C 231/12; C07C 67/347; C07C 69/612; C07C 233/08; C07C 271/14; C07D 239/42
See application file for complete search history.

(56) References Cited

U.S. PATENT DOCUMENTS 6,255,528 B1   7/2001 Müller et al.
2017/0101382 A1   4/2017 Uneme et al.

FOREIGN PATENT DOCUMENTS

| EP | 1 067 113 A2 | 1/2001 |
|----|----|----|
| JP | 2001-39931 A | 2/2001 |
| WO | WO 2015/146870 A1 | 10/2015 |

OTHER PUBLICATIONS

International Preliminary Report on Patentability and the Written Opinion of the International Searching Authority for International Application No. PCT/JP2018/020798, dated Dec. 3, 2019.
International Search Report for International Application No. PCT/JP2018/020798 dated Aug. 21, 2018.
Lebedev et al., "Condensation of Organic Bromides with Vinyl Compounds Catalysed by Nickel Complexes in the Presence of Zinc", Journal of Organometallic Chemistry, vol. 344, 1988, pp. 253-259.
Chaturvedi, "Perspectives on the synthesis of organic carbamates," Tetrahedron, vol. 68, 2012, pp. 15-45, 31 pages total.
Extended European Search Report for European Application No. 18810411.1 dated Jan. 28, 2021.
Weerman et al., "On the action of sodium hypochlorite, bromine and sodium alcoholate on hydrocinnamic amide," Recueil des Travaux Chimiques des Pays-Bas, 1906, 14 pages total, with an English translation.
Indian Examination Report for Indian Application No. 201947048599, dated Mar. 22, 2021, with an English translation.

*Primary Examiner* — Deepak R Rao
(74) *Attorney, Agent, or Firm* — Birch, Stewart, Kolasch & Birch, LLP

(57) ABSTRACT

The present invention provides a method for industrially producing: a pyrimidine compound having pest control efficacy; 2-[4-(trifluoromethyl)phenyl]ethylamine which is a production intermediate of the pyrimidine compound; a phenylethylamine compound useful as a pharmaceutical and agrochemical intermediate; and further a 3-arylpropionamide compound and a 3-arylpropionic acid ester compound useful as production intermediates of the phenylethylamine compound. The 3-arylpropionamide compound or the 3-arylpropionic acid ester compound can be efficiently and industrially produced in a single step by reacting a compound represented by formula (1)

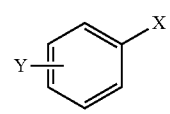

(1)

(wherein X represents a chlorine atom or a bromine atom; and Y represents an alkyl group optionally substituted with fluorine atom(s), a hydrogen atom, a fluorine atom, a cyano group, an alkylcarbonyl group, a dialkylamino group, or the like) with acrylamide or an acrylic acid ester in the presence of a metal catalyst and a reducing agent.

8 Claims, No Drawings

METHOD FOR PRODUCING 3-ARYLPROPIONAMIDE COMPOUND AND 3-ARYLPROPIONIC ACID ESTER COMPOUND

TECHNICAL FIELD

This application claims priority to and the benefits of Japanese Patent Application No. 2017-107506 filed on May 31, 2017, the entire contents of which are incorporated herein by reference.

The present invention relates to a method for producing a 3-arylpropionamide compound and a 3-arylpropionic acid ester compound, and the like.

BACKGROUND ART

Patent Document 1 discloses that 5-chloro-4-ethyl-6-[2-(4-trifluoromethylphenyl)ethylamino]pyrimidine has pest control efficacy. As an example of method for producing 5-chloro-4-ethyl-6-[2-(4-trifluoromethylphenyl)ethylamino]pyrimidine, Patent Document 1 discloses a method wherein 2-[4-(trifluoromethyl)phenyl]ethylamine is reacted with 4,5-dichloro-6-ethylpyrimidine. Thus, a phenylethylamine compound is useful as a pharmaceutical and agrochemical intermediate.

As a method for producing a phenylethylamine compound, Patent Document 2 discloses a method wherein in the first step, a fluorine-containing aryl bromide as a starting material is subjected to a Heck reaction in the presence of acrylamide and a palladium catalyst to produce a fluorine-containing 3-arylacrylamide compound; in the second step, the fluorine-containing 3-arylacrylamide compound is subjected to catalytic hydrogenation to produce a fluorine-containing 3-arylpropionamide compound; and in the third step, the fluorine-containing 3-arylpropionamide compound is subjected to a Hofmann rearrangement reaction by using bromine and an alkali metal hydroxide to produce a fluorine-containing phenylethylamine compound. In the production of the phenylethylamine compound useful as a pharmaceutical and agrochemical intermediate, it is preferable that the 3-arylacrylamide compound is efficiently produced. However, the method according to the Patent Document 2 does not an appropriate method for industrially producing the 3-arylacrylamide compound, because said method requires at least two steps from aryl bromide, and further requires using an expensive palladium catalyst, and the like, in order to produce the 3-arylacrylamide compound.

CITATION LIST

Patent Document

Patent Document 1: WO 2015/146870 pamphlet
Patent Document 2: JP 2001-39931 A

SUMMARY OF THE INVENTION

Problems to be Solved by Invention

An object for the present inventors is to provide a method for industrially producing a pyrimidine compound having pest control efficacy; 2-[4-(trifluoromethyl)phenyl]ethylamine which is a production intermediate of the pyrimidine compound; a phenylethylamine compound useful as a pharmaceutical and agrochemical intermediate; and further a 3-arylpropionamide compound and a 3-arylpropionic acid ester compound useful as production intermediates of the phenylethylamine compound.

Means to Solve Problems

The present inventors have studied to solve the above problems, and as a result found a method for producing a 3-arylpropionamide compound or a 3-arylpropionic acid ester compound in a single step by reacting a compound represented by formula (1)

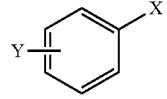

(1)

(wherein X represents a chlorine atom or a bromine atom; and Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group) with acrylamide or an acrylic acid ester in the presence of a metal catalyst and a reducing agent. The present inventors have further found that a phenylethylamine compound can be efficiently and industrially produced by subjecting a 3-arylpropionamide compound to a Hofmann rearrangement reaction.

The present inventors have also found that a 3-arylpropionamide compound can be efficiently produced also by reacting a 3-arylpropionic acid ester compound with formamide in the presence of a strong base.

Namely, the present invention provides the followings.

[1] A method for producing a compound represented by formula (2)

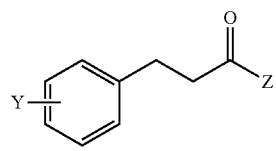

(2)

(wherein
Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group;

Z represents a $NH_2$ or a $OR^2$; and $R^2$ represents a methyl group or an ethyl group) the method comprising Step (a): reacting a compound represented by formula (1)

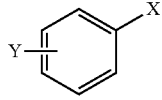
(1)

(wherein X represents a chlorine atom or a bromine atom; and Y is the same as defined above)
with a compound represented by formula (5)

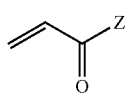
(5)

(wherein Z is the same as defined above)
in the presence of a nickel compound and zinc to produce the compound represented by formula (2).

[2] A method for producing a compound represented by formula (2a)

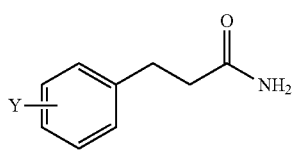
(2a)

(wherein Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group) the method comprising the following Step (a-1) and Step (b);

Step (a-1): reacting a compound represented by formula (1)

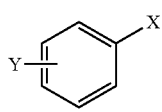
(1)

(wherein X represents a chlorine atom or a bromine atom; and Y is the same as defined above)
with a compound represented by formula (5b)

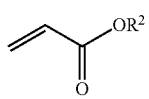
(5b)

(wherein $R^2$ represents a methyl group or an ethyl group) in the presence of a nickel compound and zinc to produce a compound represented by formula (2b)

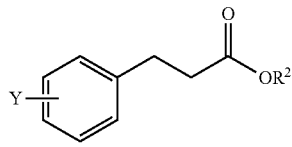
(2b)

(wherein Y and $R^2$ are the same as defined above); and Step (b): reacting the compound represented by formula (2b) with formamide in the presence of a strong base to produce the compound represented by formula (2a).

[3] A method for producing a compound represented by formula (3)

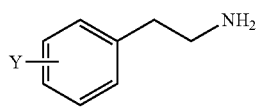
(3)

(wherein Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group)

the method comprising the following Step (a-2) or Step (c), and comprising the following Step (d):

Step (a-2): reacting a compound represented by formula (1)

(1)

(wherein X represents a chlorine atom or a bromine atom; and Y is the same as defined above)
with a compound represented by formula (5a)

(5a)

in the presence of a nickel compound and zinc to produce a compound represented by formula (2a)

(2a)

(wherein Y is the same as defined above); or

Step (c): the Step (a-1) and the Step (b) according to [2]; and

Step (d): subjecting the compound represented by formula (2a) to a Hofmann rearrangement to produce the compound represented by formula (3).

[4] The method according to [3], wherein the Step (d) is carried out in water in the presence of bromine or chlorine, and an alkali metal hydroxide.

[5] The method according to [3], wherein the Step (d) is a step of subjecting the compound represented by formula (2a) to a Hofmann rearrangement in an alcohol represented by formula (6)

$$R^1OH \quad (6)$$

(wherein $R^1$ represents a methyl group, an ethyl group, a propyl group, an isopropyl group, or a butyl group) in the presence of bromine or chlorine, and an alkali metal alcoholate compound to produce a compound represented by formula (4)

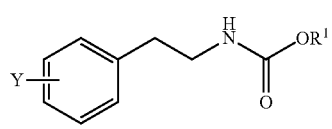

(wherein Y and $R^1$ are the same as defined above) and then reacting the compound represented by formula (4) in the presence of a strong acid to produce the compound represented by formula (3).

[6] The method according to any one of [1] to [5], wherein Y represents a 4-trifluoromethyl group.

[7] A method for producing a compound represented by formula (8)

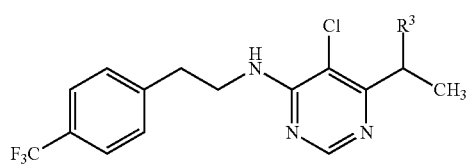

(wherein $R^3$ represents a hydrogen atom or a fluorine atom) the method comprising the Step (a-2) or the Step (c) according to any one of [3] to [5] wherein Y represents a 4-trifluoromethyl group, and comprising the Step (d), and further comprising the following Step (e):

Step (e): reacting a compound represented by formula (3a)

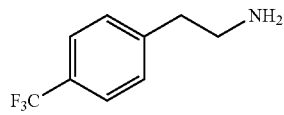

with a compound represented by formula (7)

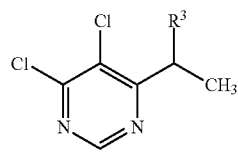

(wherein $R^3$ is the same as defined above) to produce the compound represented by formula (8).

[8] N-carbomethoxy-2-[4-(trifluoromethyl)phenyl]ethylamine.

Effect of Invention

According to the present invention, a pyrimidine compound having pest control efficacy; 2-[4-(trifluoromethyl)phenyl]ethylamine which is a production intermediate of the pyrimidine compound; a phenylethylamine compound useful as a pharmaceutical and agrochemical intermediate; and further a 3-arylpropionamide compound and a 3-arylpropionic acid ester compound useful as production intermediates of the phenylethylamine compound, can be industrially produced.

MODE FOR CARRYING OUT THE INVENTION

Hereinafter, the present invention is described in detail.

The Step (a) is described. In the Step (a), the compound represented by formula (1) is reacted with the compound represented by formula (5) in the presence of a nickel compound and zinc to produce the compound represented by formula (2).

The substituent represented by Y in the compound represented by formula (1) is not specifically limited as long as it is stable and does not disturb the reaction in the Step (a) and the Step (b).

Examples of the substituent represented by Y include an alkyl group optionally substituted with fluorine atom(s) such as a methyl group, an ethyl group, a propyl group, a butyl group, a fluoromethyl group, a difluoromethyl group, and a trifluoromethyl group; an alkoxy group optionally substituted with fluorine atom(s) such as a methoxy group, an ethoxy group, a propoxy group, a butoxy group, and a trifluoromethoxy group; an alkoxyalkyl group optionally substituted with fluorine atom(s) such as a methoxymethyl group, an ethoxymethyl group, and a trifluoromethoxymethyl group; an alkylthio group optionally substituted with fluorine atom(s) such as a thiomethyl group, a thioethyl group, a thiopropyl group, and a thiotrifluoromethyl group; an alkylsulfonyl group optionally substituted with fluorine atom(s) such as a methylsulfonyl group, an ethylsulfonyl group, and a trifluoromethylsulfonyl group; a hydrogen atom; a fluorine atom; a cyano group; an alkylcarbonyl group such as a methylcarbonyl group, an ethylcarbonyl group, and a propylcarbonyl group; a dialkylamino group such as a dimethylamino group and a diethylamino group, and preferable examples thereof include electron-withdrawing groups such as a fluorine atom, a trifluoromethyl group, an alkylcarbonyl group, and an alkylsulfonyl group.

The substitution position of Y may be any one of 2- to 4-positions, preferably 3- or 4-position, especially preferably 4-position, relative to X.

Examples of the compound represented by formula (1) include 4-methylchlorobenzene, 3-methylchlorobenzene, 4-methylbromobenzene, 3-methylbromobenzene, 4-ethylchlorobenzene, 3-ethylchlorobenzene, 4-ethylbromobenzene, 3-ethylbromobenzene, 4-propylchlorobenzene, 3-propylchlorobenzene, 4-propylbromobenzene, 3-propylbromobenzene, 4-butylchlorobenzene, 3-butylchlorobenzene, 4-butylbromobenzene, 3-butylbromobenzene, 4-(fluoromethyl) chlorobenzene, 3-(fluoromethyl) chlorobenzene, 4-(fluoromethyl) bromobenzene, 3-(fluoromethyl) bromobenzene, 4-(difluoromethyl) chlorobenzene, 3-(difluoromethyl) chlorobenzene, 4-(difluoromethyl) bromobenzene, 3-(difluoromethyl) bromobenzene, 4-(trifluoromethyl) chlorobenzene, 3-(trifluoromethyl) chlorobenzene, 4-(trifluoromethyl) bromobenzene, 3-(trifluoromethyl) bromobenzene; 4-methoxychlorobenzene, 3-methoxychlorobenzene, 4-methoxybromobenzene, 3-methoxybromobenzene, 4-ethoxychlorobenzene, 3-ethoxychlorobenzene, 4-ethoxybromobenzene, 3-ethoxybromobenzene, 4-propoxychlorobenzene, 3-propoxychlorobenzene, 4-propoxybromobenzene, 3-propoxybromobenzene, 4-butoxychlorobenzene, 3-butoxychlorobenzene, 4-butoxybromobenzene, 3-butoxybromobenzene, 4-(trifluoromethoxy) chlorobenzene, 3-(trifluoromethoxy) chlorobenzene, 4-(trifluoromethoxy) bromobenzene, 3-(trifluoromethoxy) bromobenzene; 4-(methoxymethyl) chlorobenzene, 3-(methoxymethyl) chlorobenzene, 4-(methoxymethyl) bromobenzene, 3-(methoxymethyl) bromobenzene, 4-(ethoxymethyl) chlorobenzene, 3-(ethoxymethyl) chlorobenzene, 4-(ethoxymethyl) bromobenzene, 3-(ethoxymethyl) bromobenzene, 4-(trifluoromethoxymethyl) chlorobenzene, 3-(trifluoromethoxymethyl) chlorobenzene, 4-(trifluoromethoxymethyl) bromobenzene, 3-(trifluoromethoxymethyl) bromobenzene; 4-(methylthio) chlorobenzene, 3-(methylthio) chlorobenzene, 4-(methylthio) bromobenzene, 3-(methylthio) bromobenzene, 4-(ethylthio) chlorobenzene, 3-(ethylthio) chlorobenzene, 4-(ethylthio) bromobenzene, 3-(ethylthio) bromobenzene, 4-(propylthio) chlorobenzene, 3-(propylthio) chlorobenzene, 4-(propylthio) bromobenzene, 3-(propylthio) bromobenzene, 4-(trifluoromethylthio) chlorobenzene, 3-(trifluoromethylthio) chlorobenzene, 4-(trifluoromethylthio) bromobenzene, 3-(trifluoromethylthio) bromobenzene; 4-(methylsulfonyl) chlorobenzene, 3-(methylsulfonyl) chlorobenzene, 4-(methylsulfonyl) bromobenzene, 3-(methylsulfonyl) bromobenzene, 4-(ethylsulfonyl) chlorobenzene, 3-(ethylsulfonyl) chlorobenzene, 4-(ethylsulfonyl) bromobenzene, 3-(ethylsulfonyl) bromobenzene, 4-(trifluoromethylsulfonyl) chlorobenzene, 3-(trifluoromethylsulfonyl) chlorobenzene, 4-(trifluoromethylsulfonyl) bromobenzene, 3-(trifluoromethylsulfonyl) bromobenzene; chlorobenzene, bromobenzene; 4-fluorochlorobenzene, 3-fluorochlorobenzene, 2-fluorochlorobenzene, 4-fluorobromobenzene, 3-fluorobromobenzene, 2-fluorobromobenzene; 4-cyanochlorobenzene, 3-cyanochlorobenzene, 4-cyanobromobenzene, 3-cyanobromobenzene; 4-methylcarbonylchlorobenzene, 3-methylcarbonylchlorobenzene, 4-methylcarbonylbromobenzene, 3-methylcarbonylbromobenzene, 4-ethylcarbonylchlorobenzene, 3-ethylcarbonylchlorobenzene, 4-ethylcarbonylbromobenzene, 3-ethylcarbonylbromobenzene, 4-propylcarbonylchlorobenzene, 3-propylcarbonylchlorobenzene, 4-propylcarbonylbromobenzene, 3-propylcarbonylbromobenzene; 4-(dimethylamino) chlorobenzene, 3-(dimethylamino) chlorobenzene, 4-(dimethylamino) bromobenzene, 3-(dimethylamino) bromobenzene, 4-(diethylamino) chlorobenzene, 3-(diethylamino) chlorobenzene, 4-(diethylamino) bromobenzene, and 3-(diethylamino) bromobenzene.

The amount of the compound represented by formula (5) to be used is usually 1.0 to 5.0 mol, preferably 1.5 to 3.0 mol, relative to 1 mol of the compound represented by formula (1).

Examples of the nickel compound include nickel salts. Specific examples thereof include halogenated nickels such as nickel chloride and nickel bromide. The nickel compound may be used in the form of anhydride or hydrate. Examples of the nickel compound in the form of hydrate include nickel chloride hexahydrate and nickel bromide trihydrate.

The amount of the nickel compound to be used is usually 0.01 to 0.5 mol, preferably 0.05 to 0.2 mol, relative to 1 mol of the compound represented by formula (1).

The zinc is preferably used in a powdery state.

The amount of the zinc to be used is usually 0.9 to 5 mol, preferably 1.0 to 3.0 mol, relative to 1 mol of the compound represented by formula (1).

The reaction is usually carried out in a solvent.

Examples of the solvent include ethers such as tetrahydrofuran, 2-methyltetrahydrofuran, cyclopentyl methyl ether, tert-butyl methyl ether, monoglyme, and diglyme; amides such as N,N-dimethylacetamide, N,N-dimethylformamide, and N-methylpyrrolidone; nitrogen-containing aromatic compounds such as pyridine, 2-methylpyridine, picoline, and quinoline; nitriles such as acetonitrile and propylnitrile; and mixed solvents thereof. Preferable examples thereof include amides, nitrogen-containing aromatic compounds, and mixed solvents thereof.

The amount of the solvent to be used is usually 1 to 100 part(s) by weight, preferably 1 to 30 part(s) by weight, relative to 1 part by weight of the compound represented by formula (1).

Addition of a compound which may be coordinated to the nickel compound can suppress the production of a by-product which is a compound represented by formula (1) wherein X is replaced with a hydrogen atom to improve the yield of the compound represented by formula (2).

Examples of the compound which may be coordinated to the nickel compound include alkylamines such as N,N,N',N'-tetramethylethylenediamine, N,N,N',N'-tetraethylethylenediamine, trimethylamine, triethylamine, and N,N,N',N'-tetramethylpropylenediamine; phosphines such as triphenylphosphine, 1,2-bis(diphenylphosphino)ethane, and 1,3-bis(diphenylphosphino)propane; and nitrogen-containing aromatic compounds such as pyridine, 2,2'-bipyridyl, and phenanthroline. When a halogenated nickel is used as the nickel compound, an alkylamine is preferably used. The amount of the compound which may be coordinated to the nickel compound to be used is usually 0.9 to 5 mol, preferably 1.0 to 3.0 mol, relative to 1 mol of the nickel compound.

In order to activate the zinc, an acid may be added to the reaction at the time of reaction initiation. Examples of the acid include acetic acid, trifluoroacetic acid, hydrochloric acid, and sulfuric acid, and preferable examples thereof include trifluoroacetic acid. The amount of the acid to be used is usually 0.0001 to 0.01 mol relative to 1 mol of the zinc.

The reaction temperature is usually within the range of 20 to 150° C., preferably 40 to 100° C.

The reaction time is within the range of 0.1 to 48 hour(s).

Although embodiments of the reaction are not specifically limited, the reaction is usually carried out by a method wherein the nickel compound, the compound which may be coordinated to the nickel compound, and the solvent are mixed, then the compound represented by formula (1), the compound represented by formula (5), and the zinc are added thereto, and finally the acid is added thereto to initiate the reaction.

After the reaction is completed, for example, the nickel compound and the zinc are removed by filtration; or a strong acid such as hydrochloric acid is added to the reaction to change the zinc into a water-soluble compound, then the resulting mixture is diluted with organic solvent(s), the resulting aqueous layer(s) is/are separated, further the resulting organic layer(s) is/are washed with water, and then organic solvent(s) is/are distilled away; or the like, to produce the compound represented by formula (2). The resulting compound may be further purified by distillation, column chromatography, or the like.

The Step (a-1) is described. In the Step (a-1), the compound represented by formula (1) is reacted with the compound represented by formula (5b) in the presence of a nickel compound and zinc to produce the compound represented by formula (2b).

While the reaction may be carried out according to the same method as the Step (a) by using the compound represented by formula (5b) instead of the compound represented by formula (5), the yield of the compound represented by formula (2b) is improved in the present reaction by further adding a hydrogen ion source thereto.

Examples of the hydrogen ion source include alcohols such as methanol, ethanol, propanol, and butanol; amides such as formamide, acetamide, and 2-pyrrolidone; and ketones such as acetone and methyl isobutyl ketone. Preferable examples thereof include methyl isobutyl ketone.

The amount of the hydrogen ion source to be used is usually 0.8 to 5.0 mol, preferably 0.8 to 1.2 mol, relative to 1 mol of the compound represented by formula (1).

The Step (b) is described. In the Step (b), the compound represented by formula (2b) is reacted with formamide in the presence of a strong base to produce the compound represented by formula (2a).

The amount of the formamide to be used is usually 0.9 to 10 mol, preferably 1.0 to 4 mol, relative to 1 mol of the compound represented by formula (2b).

Examples of the strong base include alkali metal alcoholate compounds. Examples of the alkali metal alcoholate compound include alkali metal methylates such as lithium methylate, sodium methylate, and potassium methylate; alkali metal propoxides such as lithium n-propoxide, sodium isopropoxide, and potassium n-propoxide; and alkali metal butoxides such as lithium n-butoxide, sodium t-butoxide, and potassium t-butoxide, preferable examples thereof include alkali metal methylates, and especially preferable examples thereof include sodium methylate.

The amount of the strong base such as alkali metal alcoholate compounds to be used is usually 1 to 15 mol, preferably 2 to 8 mol, relative to 1 mol of the compound represented by formula (2b).

The reaction is usually carried out by using an alcohol as a solvent.

Examples of the alcohol to be used as a solvent include methanol, ethanol, propanol, isopropyl alcohol, butanol, and t-butyl alcohol.

A solution of the alkali metal alcoholate compound in the alcohol may be used in the reaction.

The amount of the solvent to be used is usually 1 to 100 part(s) by weight, preferably 1 to 30 part(s) by weight, relative to 1 part by weight of the compound represented by formula (2b).

The reaction temperature is usually within the range of 0 to 100° C., preferably 25 to 60° C. When t-butyl alcohol is used as a solvent, the reaction temperature is usually within the range of 25 to 100° C., preferably 25 to 60° C.

The reaction time is within the range of 0.1 to 24 hour(s).

Although embodiments of the reaction are not specifically limited, the reaction is usually carried out by a method wherein the compound represented by formula (2b), the alkali metal alcoholate compound, and the solvent are mixed, then formamide is added thereto, and the resulting mixture is heated to a desired temperature.

After the reaction is completed, for example, the solvent is distilled away, then the resulting mixture is diluted with water and organic solvent(s) to be used for separation, washed with water, extracted, and the organic solvent(s) is/are distilled away to produce the compound represented by formula (2a). The compound represented by formula (2a) may be further purified by distillation, column chromatography, or the like.

The Step (a-2) is described. In the Step (a-2), the compound represented by formula (1) is reacted with the compound represented by formula (5a) in the presence of a nickel compound and zinc to produce the compound represented by formula (2a).

The reaction may be carried out according to the same method as the Step (a) by using the compound represented by formula (5a) instead of the compound represented by formula (5).

The Step (c) is described. The Step (c) consists of the Step (a-1) and the Step (b).

The Step (d) is described. The Step (d) comprises subjecting the compound represented by formula (2a) to a Hofmann rearrangement reaction to produce the compound represented by formula (3).

The Hofmann rearrangement reaction may be carried out by using water or alcohol as a solvent in the presence of bromine or chlorine, and a base. Specific examples thereof include:

(1) a method wherein the compound represented by formula (2a) is reacted in water in the presence of bromine or chlorine, and an alkali metal hydroxide to produce the compound represented by formula (3); and (2) a method wherein the compound represented by formula (2a) is reacted in the alcohol represented by formula (6) in the presence of bromine or chlorine, and an alkali metal alcoholate compound to produce the compound represented by formula (4).

In the method according to (2), the compound represented by formula (4) is produced, and the resulting compound represented by formula (4) is subsequently reacted in the presence of a strong acid to produce the compound represented by formula (3).

First, a method wherein the compound represented by formula (2a) is subjected to a Hofmann rearrangement reaction in water in the presence of bromine or chlorine, and an alkali metal hydroxide to produce the compound represented by formula (3), is described.

The amount of the bromine or chlorine to be used is usually 0.9 to 3 mol, preferably 1.0 to 1.5 mol, relative to 1 mol of the compound represented by formula (2a).

Examples of the alkali metal hydroxide include lithium hydroxide, sodium hydroxide, and potassium hydroxide. The amount of the alkali metal hydroxide to be used is usually 1 to 15 mol, preferably 2 to 8 mol, relative to 1 mol of the compound represented by formula (2a).

The reaction may also be carried out by using an alkali metal salt of hypobromous acid or hypochlorous acid, preferably sodium hypobromite or sodium hypochlorite instead of mixing the bromine or chlorine, and the alkali metal hydroxide in water. The amount of the sodium hypobromite or sodium hypochlorite to be used is the same as the amount of the bromine or chlorine to be used.

Water is used as a solvent.

The amount of the water to be used is usually 1 to 100 part(s) by weight, preferably 1 to 30 part(s) by weight, relative to 1 part by weight of the compound represented by formula (2a).

The reaction temperature is usually within the range of 20 to 150° C., preferably 40 to 120° C.

The reaction time is within the range of 0.1 to 24 hour(s).

Although embodiments of the reaction are not specifically limited, the reaction is usually carried out by a method wherein the compound represented by formula (2a), the alkali metal hydroxide, and water are mixed, then bromine or chlorine are added thereto, and the resulting mixture is heated to a desired temperature.

After the reaction is completed, for example, the reaction mixture is diluted with organic solvent(s), extracted, and the organic solvent(s) is/are distilled away to produce the compound represented by formula (3). The compound represented by formula (3) may be further purified by distillation, column chromatography, or the like.

Next, a method wherein the compound represented by formula (2a) is subjected to a Hofmann rearrangement reaction in the alcohol represented by formula (6) in the presence of bromine or chlorine, and an alkali metal alcoholate compound to produce the compound represented by formula (4), and then the resulting compound represented by formula (4) is reacted in the presence of a strong acid to produce the compound represented by formula (3), is described.

The amount of the bromine or chlorine to be used is usually 0.9 to 3 mol, preferably 1.0 to 1.5 mol, relative to 1 mol of the compound represented by formula (2a).

Examples of the alkali metal alcoholate compound include alkali metal methylates such as lithium methylate, sodium methylate, and potassium methylate; alkali metal propoxides such as lithium n-propoxide, sodium isopropoxide, and potassium n-propoxide; and alkali metal butoxides such as lithium n-butoxide, sodium t-butoxide, and potassium t-butoxide. Preferable examples thereof include alkali metal methylates, and especially preferable examples thereof include sodium methylate.

The amount of the alkali metal alcoholate compound to be used is usually 1 to 15 mol, preferably 2 to 8 mol, relative to 1 mol of the compound represented by formula (2a).

Examples of the alcohol represented by formula (6) used as a solvent include methanol, ethanol, propanol, isopropyl alcohol, and butanol.

The amount of the alcohol represented by formula (6) to be used is usually 1 to 100 part(s) by weight, preferably 1 to 30 part(s) by weight, relative to 1 part by weight of the compound represented by formula (2a).

In the reaction, other solvent(s) such as chlorobenzene may also be present.

The reaction temperature is usually within the range of 20 to 150° C., preferably 40 to 100° C.

The reaction time is within the range of 0.1 to 24 hour(s).

Although embodiments of the reaction are not specifically limited, the reaction is usually carried out by a method wherein the compound represented by formula (2a), the alkali metal alcoholate compound, and the alcohol represented by formula (6) are mixed, then bromine or chlorine are added thereto, and the resulting mixture is heated to a desired temperature.

After the reaction is completed, for example, the alcohol is distilled away, then the resulting mixture is diluted with water and organic solvent(s) to be used in separation, washed with water, extracted, and the organic solvent(s) is/are distilled away to produce the compound represented by formula (0.4). The compound represented by formula (4) may be further purified by distillation, column chromatography, or the like.

Subsequently, the compound represented by formula (4) is reacted in the presence of a strong acid to produce the compound represented by formula (3).

Examples of the strong acid include hydrochloric acid, sulfuric acid, and phosphoric acid.

The amount of the strong acid to be used is usually 1 to 15 mol, preferably 2 to 8 mol, relative to 1 mol of the compound represented by formula (4).

Although it is not necessary to use a solvent in the reaction, a solvent which does not disturb the reaction may be used.

The reaction temperature is usually within the range of 20 to 150° C., preferably 40 to 100° C.

The reaction time is within the range of 0.1 to 100 hour(s).

Preferable embodiments of the reaction include a method wherein the compound represented by formula (4), the strong acid, and if necessary a solvent are mixed, then the resulting mixture is heated to a desired temperature, and the eliminated alcohol is distilled away from a reaction container under reduced pressure or normal pressure.

After the reaction is completed, for example, the reaction mixture is diluted with organic solvent(s), neutralized and washed with alkali water, then extracted, and the organic solvent(s) is/are distilled away to produce the compound represented by formula (3). The compound represented by formula (3) may be further purified by distillation, column chromatography, or the like.

The Step (e) is described. The compound represented by formula (3a) (namely, 2-[4-(trifluoromethyl)phenyl]ethylamine) is reacted with the compound represented by formula (7) to produce the compound represented by formula (8).

The compound represented by formula (7) is available as a commercialized product. Alternatively, the compound represented by formula (7) may be produced according to the method described in, for example, U.S. Pat. No. 5,523,404A.

The reaction is usually carried out in a solvent.

Examples of the solvent include alcohols such as methanol, ethanol, and isopropanol; aromatic hydrocarbons such as toluene, xylene, cumene, monochlorobenzene, and tetralin; hydrocarbons such as hexane, heptane, octane, nonane, and cyclohexane; sulfur-containing compounds such as dimethyl sulfoxide and sulfolane; ethers such as tetrahydrofuran, 2-methyltetrahydrofuran, cyclopentyl methyl ether, tert-butyl methyl ether, monoglyme, and diglyme; amides such as N,N-dimethylacetamide, N,N-dimethylformamide, and N-methylpyrrolidone; nitriles such as acetonitrile and propylnitrile; water; and mixed solvents thereof. Preferable examples thereof include aromatic hydrocarbons and amides.

The amount of the solvent to be used is usually 1 to 100 part(s) by weight, preferably 1 to 30 part(s) by weight, relative to 1 part by weight of the compound represented by formula (3a).

The amount of the compound represented by formula (7) to be used is usually 0.5 to 3 mol, preferably 0.8 to 1.5 mol, relative to 1 mol of the 2-[4-(trifluoromethyl)phenyl]ethylamine.

The present reaction is usually carried out in the presence of a base.

Examples of the base include alkali metal hydrides such as sodium hydride; carbonates such as sodium carbonate, potassium carbonate, and cesium carbonate; alkali metal hydroxides such as sodium hydroxide, potassium hydroxide, and lithium hydroxide; metal alcoholates such as sodium methylate, sodium ethylate, sodium tert-butoxide, potassium methylate, potassium ethylate, and potassium tert-butoxide; and organic amines such as triethylamine, diisopropylethylamine, pyridine, and diazabicycloundecene.

The amount of the base to be used is usually 1 to 5 mol relative to 1 mol of the compound represented by formula (7).

The reaction may be carried out in the presence of a phase-transfer catalyst. Examples of the phase-transfer catalyst include tetrabutyl ammonium bromide and triethylbenzyl ammonium chloride. The amount of the phase-transfer catalyst to be used is 0.01 to 0.5 mol relative to 1 mol of the compound represented by formula (7).

The reaction temperature is usually within the range of 0° C. to 150° C., preferably 0° C. to 100° C.

The reaction time is within the range of 0.1 to 48 hour(s).

After the reaction is completed, for example, water is added to the reaction mixture, the resulting mixture is extracted with organic solvent(s), and the organic solvent(s) is/are distilled away to isolate the compound represented by formula (8). The compound represented by formula (8) may be further purified by crystallization, column chromatography, or the like.

Examples of the compound represented by formula (8) include 5-chloro-4-ethyl-6-[2-(4-trifluoromethylphenyl)ethylamino]pyrimidine and 5-chloro-4-(1-fluoroethyl)-6-[2-(4-trifluoromethylphenyl)ethylamino]pyrimidine.

EXAMPLES

The following Examples etc. serve to illustrate the present invention, which should not intend to limit the present invention.

High performance liquid chromatography measurement conditions

Measuring instrument: LC-20AD manufactured by Shimadzu Corporation

Mobile phase: Solution A: 0.1% phosphoric acid aqueous solution, Solution B: acetonitrile Column: SUMIPAX (registered trademark) ODS Z-CLUE (manufactured by Sumika Chemical Analysis Service, Ltd.) Inner diameter: 4.6 mm, Length: 100 mm, particle size 3 μm Column temperature: 40° C.
Flow rate: 1.0 mL/min
UV wavelength: 265 nm
Injection volume: 5 μL
Internal standard material: dimethyl phthalate
Time program

| Time (min) | B conc (%) |
|---|---|
| 0 | 0 |
| 40 | 100 |
| 50 | 100 |
| 50.1 | 5 |
| 60 | 5 |

Gas chromatography measurement conditions

Measuring instrument: GC-2010 manufactured by Shimadzu Corporation

Column: DB-5, Length: 30 m, Inner diameter: 250 μm, Film thickness: 1.00 μm (manufactured by Agilent Technologies, Inc.)

Column temperature: warmed from 150° C. to 320° C. at 10° C./min, then maintained at 320° C. for 10 minutes Helium gas flow rate: 1.0 mL/min
Injection volume: 1 μL

Example 1

Under nitrogen atmosphere in a four neck flask (200 mL), nickel chloride anhydride (5.74 g), N,N,N',N'-tetramethylethylenediamine (5.10 g), and N,N-dimethylformamide (79.2 g) were mixed, and the resulting mixture was warmed to 80° C. The mixture was stirred at the same temperature for 1 hour, then acrylamide (23.4 g) and 4-chlorobenzotrifluoride (40.0 g) were added thereto, and the resulting mixture was cooled to 60° C. Zinc powder (28.7 g) was added thereto over 30 minutes, then the resulting mixture was stirred at the same temperature for 48 hours. A part of the reaction mixture was sampled and analyzed by a gas chromatography area normalization method to confirm that the mixture included 3-[4-(trifluoromethyl)phenyl]propionamide (77%), 4-chlorobenzotrifluoride (0.5%), and trifluoromethylbenzene (13%) which was a dechlorinated product of the starting material. The reaction mixture was cooled to room temperature, added dropwise to 24% hydrochloric acid water (131 g) controlled at 15° C., and then the resulting mixture was stirred for 2 hours. To the resulting reaction mixture was added sodium chloride (39.9 g), and the resulting mixture was extracted twice with a mixed solvent (118.8 g) of ethyl acetate and chlorobenzene (2:1). The resulting oil layer was washed with water (118.8 g), and then analyzed by an internal reference method using high performance liquid chromatography to confirm that the yield of 3-[4-(trifluoromethyl)phenyl]propionamide was 69.4%.

Example 2

Under nitrogen atmosphere in a Schlenk flask (50 mL), nickel chloride anhydride (230 mg), N,N,N',N'-tetramethylethylenediamine (207 mg), and N,N-dimethylformamide (2 g) were mixed, and the resulting mixture was warmed to 80° C. The mixture was stirred at the same temperature for 1 hour, then acrylamide (950 mg) and chlorobenzene (1.0 g) were added thereto, and the resulting mixture was cooled to 60° C. Zinc powder (1.16 g) was added thereto, and then the resulting mixture was stirred at the same temperature for 8 hours. A part of the reaction mixture was sampled and analyzed by a gas chromatography area normalization method to confirm that the mixture included 3-phenylpropionamide (73%) and chlorobenzene (27%). The reaction mixture was cooled to room temperature, 24% hydrochloric acid water (10 g) was added thereto, and then the resulting mixture was stirred for 2 hours. To the resulting reaction mixture was added sodium chloride (5 g), and the resulting mixture was extracted twice with ethyl acetate (10 g). The resulting oil layer was washed with water (10 g), and then the solvent was distilled away to give 3-phenylpropionamide as white crystals (1.02 g). The yield was 77.0%.

Example 3

Under nitrogen atmosphere in a Schlenk flask (50 mL), nickel chloride anhydride (132 mg), N,N,N',N'-tetramethylethylenediamine (119 mg), and N,N-dimethylformamide (1.2 g) were mixed, and the resulting mixture was warmed to 80° C. The mixture was stirred at the same temperature for 1 hour, then acrylamide (542 mg) and 3-trifluoromethoxychlorobenzene (1.0 g) were added thereto, and the resulting mixture was cooled to 60° C. Zinc powder (666 mg) was added thereto, and then the resulting mixture was stirred at the same temperature for 8 hours. A part of the reaction mixture was sampled and analyzed by a gas chromatography area normalization method to confirm that the mixture included 3-[3-(trifluoromethoxy)phenyl]propionamide (34%) and 3-trifluoromethoxychlorobenzene (66%). The reaction mixture was cooled to room temperature, 24% hydrochloric acid water (10 g) was added thereto, and then the resulting mixture was stirred for 2 hours. To the resulting reaction mixture was added sodium chloride (5 g), and the resulting mixture was extracted twice with ethyl acetate (10 g). The resulting oil layer was washed with water (10 g), and then the solvent was distilled away to give 3-[3-(trifluoromethoxy)phenyl]propionamide as white crystals (990 mg). The yield was 41.0%.

Example 4

Under nitrogen atmosphere in a Schlenk flask (50 mL), nickel chloride anhydride (200 mg), N,N,N',N'-tetramethylethylenediamine (180 mg), and N,N-dimethylformamide (1.8 g) were mixed, and the resulting mixture was warmed to 80° C. The mixture was stirred at the same temperature for 1 hour, then acrylamide (820 mg) and 2-fluorochlorobenzene (1.0 g) were added thereto, and the resulting mixture was cooled to 60° C. Zinc powder (1.0 g) was added thereto, and then the resulting mixture was stirred at the same temperature for 8 hours. A part of the reaction mixture was sampled and analyzed by a gas chromatography area normalization method to confirm that the mixture included 3-[2-(fluoro)phenyl]propionamide (3%) and 2-fluorochlorobenzene (97%). The reaction mixture was cooled to room temperature, 24% hydrochloric acid water (10 g) was added thereto, and then the resulting mixture was stirred for 2 hours. To the resulting reaction mixture was added sodium chloride (5 g), and the resulting mixture was extracted twice with ethyl acetate (10 g). The resulting oil layer was washed with water (10 g), and then the solvent was distilled away to give 3-[2-(fluoro)phenyl]propionamide as white crystals (51 mg). The yield was 4.0%.

Example 5

Under nitrogen atmosphere in a four neck flask (500 mL), nickel chloride anhydride (5.82 g), pyridine (11.6 g), and N,N-dimethylformamide (116.4 g) were mixed, and the resulting mixture was stirred at room temperature for 5 minutes. Ethyl acrylate (66.5 g), 4-chlorobenzotrifluoride (40.0 g), zinc powder (29.0 g), and methyl isobutyl ketone (16.1 g) were sequentially added thereto at the same temperature, and then the resulting mixture was heated to 100° C. Trifluoroacetic acid (0.25 g) was added thereto, and then the resulting mixture was stirred at the same temperature for 6 hours. A part of the reaction mixture was sampled and analyzed by a gas chromatography area normalization method to confirm that the mixture included ethyl 3-[4-(trifluoromethyl)phenyl]propionate (63%), 4-chlorobenzotrifluoride (0.1%), and trifluoromethylbenzene (5.4%) which was a dechlorinated product of the starting material. The reaction mixture was cooled to room temperature, added dropwise to 20% hydrochloric acid (161.6 g) cooled in an ice bath, and then the resulting mixture was filtered. The resulting filtrate was controlled at 40° C., and the resulting mixture was extracted twice with toluene (120 g). The resulting oil layer was washed with water (40.0 g), and then concentrated under reduced pressure. The resulting yellow oil was analyzed by an internal reference method using high performance liquid chromatography to confirm that the yield of ethyl 3-[4-(trifluoromethyl)phenyl]propionate was 68.8%.

Example 6

Under nitrogen atmosphere, ethyl 3-[4-(trifluoromethyl)phenyl]propionate (66.0 g), a 28% solution of sodium methylate in methanol (41.9 g), and formamide (19.2 g) were mixed, and the resulting mixture was heated at 50° C. The mixture was stirred at the same temperature for 4 hours, then formamide (6.26 g) was additionally added thereto, and the resulting mixture was stirred for additional 1 hour. A part of the reaction mixture was sampled and analyzed by a gas chromatography area normalization method to confirm that the mixture included 3-[4-(trifluoromethyl)phenyl]propionamide (47%) and ethyl 3-[4-(trifluoromethyl)phenyl]propionate (2.7%). The reaction solution was concentrated under reduced pressure, then neutralized with 10% hydrochloric acid (76.0 g), and the resulting mixture was extracted twice with ethyl acetate (102.6 g). The resulting oil layer was concentrated under reduced pressure to give a brownish-red crude product (65.2 g). The product was analyzed by an internal reference method using high performance liquid chromatography to confirm that the yield of 3-[4-(trifluoromethyl)phenyl]propionamide was 97.0%.

Example 7

Under nitrogen atmosphere, 3-[4-(trifluoromethyl)phenyl]propionamide (500 mg) and a 28% solution of sodium methylate in methanol (2.8 g) were mixed, and the resulting mixture was cooled in a water bath. To the mixture was added dropwise bromine (410 mg), and then the resulting mixture was stirred at 60° C. for 3 hours. The reaction mixture was cooled to room temperature, water (10 g) was added thereto, and then the resulting mixture was extracted twice with ethyl acetate (10 g). The resulting oil layer was concentrated to give a pale yellow oil (510 mg). Said oil was analyzed by $^1$H-NMR and GC-MS to be identified as N-carbomethoxy-2-[4-(trifluoromethyl)phenyl]ethylamine. The yield was 90%. $^1$H-NMR (CDCl$_3$) δ (ppm): 7.51 (2H, dd), 7.30 (2H, dd), 4.24 (1H, bs), 3.18 (3H, s), 2.98 (2H, dd), 2.41 (2H, dd). GC-MS: [M$^+$] 247.

Example 8

Under nitrogen atmosphere, 3-[4-(trifluoromethyl)phenyl]propionamide (34.1 g) and a 28% solution of sodium methylate in methanol (68.6 g) were mixed, and the resulting mixture was heated to 45° C. To the mixture was added dropwise bromine (30.0 g), and then the resulting mixture was stirred at the same temperature for 5 hours. The reaction mixture was cooled to room temperature, a saturated aqueous solution of sodium sulfite (43.0 g) and sulfuric acid (0.42 g) were added thereto, the resulting mixture was concentrated under reduced pressure, and then subjected to azeotropic dehydration with xylene (30.9 g). To the resulting concentrate were added water (35.2 g) and sulfuric acid (18.2 g), and the resulting mixture was heated to 95° C. After starting the incubation at the same temperature, sulfuric acid (5.6 g) was additionally added thereto at 8, 17, 28, and 48 hours, respectively, and the resulting mixture was stirred for 70 hours in total. A part of the reaction mixture was sampled and analyzed by a gas chromatography area normalization method to confirm that the mixture included 2-[4-(trifluoromethyl)phenyl]ethylamine (94.9%) and N-carbomethoxy-2-[4-(trifluoromethyl)phenyl]ethylamine (2.7%). To the reaction mixture was added chlorobenzene, the resulting mixture was cooled to room temperature, added dropwise to a 14% aqueous solution of sodium hydroxide (246 g), and then the resulting mixture was separated at 40° C. The resulting oil layer was washed with water (30.9 g), and then the oil layer was analyzed by an internal reference method using high performance liquid chromatography to confirm that the yield of 2-[4-(trifluoromethyl)phenyl]ethylamine was 78%.

Example 9

Under nitrogen atmosphere, 3-[4-(trifluoromethyl)phenyl]propionamide (25.1 g), chlorobenzene (50.2 g), and a 28% solution of sodium methylate in methanol (55.7 g) were mixed, and the resulting mixture was heated to 45° C. To the mixture was added dropwise bromine (20.4 g), and then the resulting mixture was stirred at the same temperature for 4 hours. The reaction mixture was cooled to room temperature, then a 15% aqueous solution of sodium sulfite (21.4 g) and sulfuric acid (1.74 g) were added thereto, and the resulting mixture was concentrated under reduced pressure. The resulting concentrate, water (30.1 g), and sulfuric acid (17.3 g) were mixed, and the resulting mixture was heated to 95° C. After starting the incubation at the same temperature, sulfuric acid (5.8 g) was additionally added thereto at 10, 20, and 36 hours, respectively, and the resulting mixture was stirred for 52 hours in total. A part of the reaction mixture was sampled and analyzed by a gas chromatography area normalization method to confirm that the mixture included 2-[4-(trifluoromethyl)phenyl]ethylamine (88.4%) and N-carbomethoxy-2-[4-(trifluoromethyl)phenyl]ethylamine (6.8%). To the reaction mixture was added xylene (100.3 g), the resulting mixture was cooled to room temperature, added dropwise to a 20% aqueous solution of sodium hydroxide (170.7 g), and then the resulting mixture was separated at 60° C. The resulting oil layer was washed with water (25.1 g), and then analyzed by an internal reference method using high performance liquid chromatography to confirm that the yield of 2-[4-(trifluoromethyl)phenyl]ethylamine was 62%.

Example 10

Under nitrogen atmosphere, to a mixture of 3-[4-(trifluoromethyl)phenyl]propionamide (4.9 g) and a 20% aqueous solution of sodium hydroxide (27.5 g) was added dropwise bromine (4.0 g), and the resulting mixture was stirred at 100° C. for 3 hours. The reaction mixture was cooled to room temperature, water (100 g) was added thereto, and then the resulting mixture was extracted twice with ethyl acetate (100 g). The resulting oil layer was concentrated, and then distilled under reduced pressure to give a colorless and transparent liquid of 2-[4-(trifluoromethyl)phenyl]ethylamine (1.9 g, yield: 48%) as the main distillate.

Example 11

Under nitrogen atmosphere in a separable flask (200 mL), potassium carbonate (5.9 g), N,N-dimethylformamide (15.3 g), and water (0.4 g) were mixed, and the resulting mixture was warmed to 60° C. To the resulting mixture were simultaneously and separately added dropwise 2-[4-(trifluoromethyl)phenyl]ethylamine (7.9 g) and 4,5-dichloro-6-ethylpyrimidine (a 37% by weight solution in xylene, 20.5 g), and the resulting mixture was stirred at the same temperature for 6 hours. The resulting reaction mixture, water (30.6 g), and xylene (11.1 g) were mixed, and the resulting mixture was separated at 55° C. The resulting oil layer was washed twice with water (15.3 g), then crystallized by evaporation, and the resulting solids were collected by filtration. The resulting solids were washed with water (15.3 g), and then dried under reduced pressure to give 5-chloro-4-ethyl-6-[2-(4-trifluoromethylphenyl)ethylamino]pyrimidine (11.6 g, yield: 86%).

INDUSTRIAL APPLICABILITY

According to the present invention, a pyrimidine compound having pest control efficacy; 2-[4-(trifluoromethyl)phenyl]ethylamine which is a production intermediate of the pyrimidine compound; a phenylethylamine compound useful as a pharmaceutical and agrochemical intermediate; and further a 3-arylpropionamide compound and a 3-arylpropionic acid ester compound useful as production intermediates of the phenylethylamine compound, can be industrially produced.

The invention claimed is:

1. A method for producing a compound represented by formula (2)

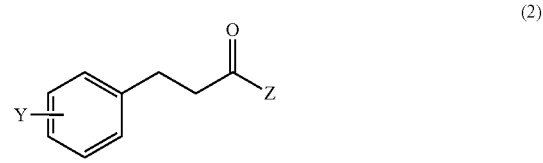

(wherein
Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group; and
Z represents a NH$_2$
the method comprising
Step (a): reacting a compound represented by formula (1)

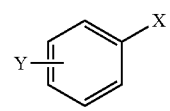

(wherein X represents a chlorine atom; and Y is the same as defined above)

with a compound represented by formula (5)

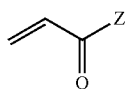

(wherein Z is the same as defined above)
in the presence of a nickel compound and zinc to produce the compound represented by formula (2).

2. A method for producing a compound represented by formula (2a)

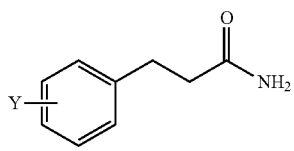

(wherein Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group)

the method comprising the following Step (a-1) and Step (b);

Step (a-1): reacting a compound represented by formula (1)

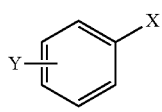

(wherein X represents a chlorine atom; and Y is the same as defined above)

with a compound represented by formula (5b)

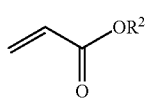

(wherein R² represents a methyl group or an ethyl group) in the presence of a nickel compound and zinc to produce a compound represented by formula (2b)

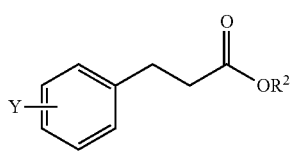

(wherein Y and R² are the same as defined above); and

Step (b): reacting the compound represented by formula (2b) with formamide in the presence of a strong base to produce the compound represented by formula (2a).

3. A method for producing a compound represented by formula (3)

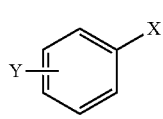

(wherein Y represents an alkyl group optionally substituted with fluorine atom(s), an alkoxy group optionally substituted with fluorine atom(s), an alkoxyalkyl group optionally substituted with fluorine atom(s), an alkylthio group optionally substituted with fluorine atom(s), an alkylsulfonyl group optionally substituted with fluorine atom(s), a hydrogen atom, a fluorine atom, a cyano group, an alkylcarbonyl group, or a dialkylamino group)

the method comprising the following Step (a-2) or Step (c), and comprising the following Step (d):

Step (a-2): reacting a compound represented by formula (1)

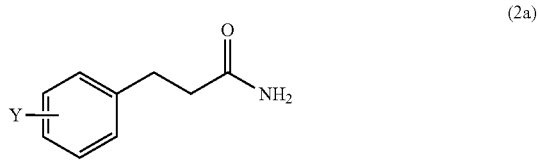

(wherein X represents a chlorine atom; and Y is the same as defined above)

with a compound represented by formula (5a)

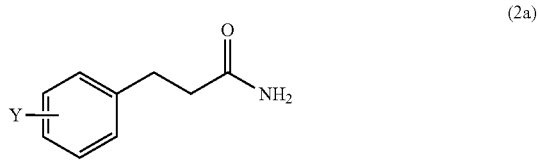

in the presence of a nickel compound and zinc to produce a compound represented by formula (2a)

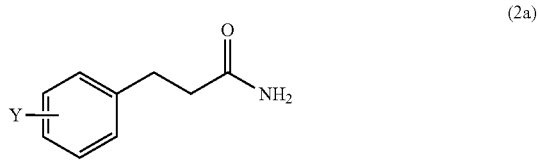

(wherein Y is the same as defined above); or

Step (c): the following Step (a-1) and the following Step (b)

Step (a-1): reacting a compound represented by formula (1)

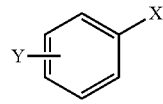

(wherein X represents a chlorine atom; and Y is the same as defined above)
with a compound represented by formula (5b)

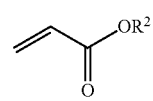

(wherein $R^2$ represents a methyl group or an ethyl group) in the presence of a nickel compound and zinc to produce a compound represented by formula (2b)

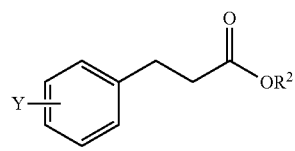

(wherein Y and $R^2$ are the same as defined above); and
Step (b): reacting the compound represented by formula (2b) with formamide in the presence of a strong base to produce a compound represented by formula (2a)

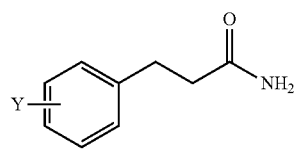

(wherein Y is the same as defined above); and
Step (d): subjecting the compound represented by formula (2a) to a Hofmann rearrangement to produce the compound represented by formula (3).

4. The method according to claim 3, wherein the Step (d) is carried out in water in the presence of bromine or chlorine, and an alkali metal hydroxide.

5. The method according to claim 3, wherein the Step (d) is a step of
subjecting the compound represented by formula (2a) to a Hofmann rearrangement in an alcohol represented by formula (6)

$R^1OH$           (6)

(wherein $R^1$ represents a methyl group, an ethyl group, a propyl group, an isopropyl group, or a butyl group) in the presence of bromine or chlorine, and an alkali metal alcoholate compound to produce a compound represented by formula (4)

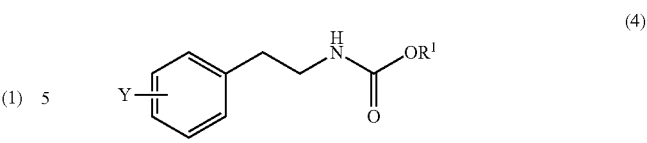

(wherein Y and $R^1$ are the same as defined above)
and then
reacting the compound represented by formula (4) in the presence of a strong acid to produce the compound represented by formula (3).

6. The method according to claim 1, wherein Y represents a 4-trifluoromethyl group.

7. A method for producing a compound represented by formula (8)

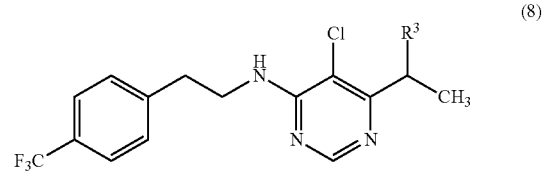

(wherein $R^3$ represents a hydrogen atom or a fluorine atom)
the method comprising the following Step (a-2) or the following Step (c)
Step (a-2): reacting a compound represented by formula (1)

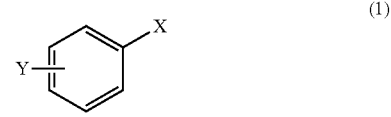

(wherein X represents a chlorine atom; and Y represents a 4-trifluoromethyl group)
with a compound represented by formula (5a)

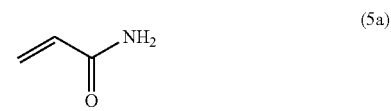

in the presence of a nickel compound and zinc to produce a compound represented by formula (2a)

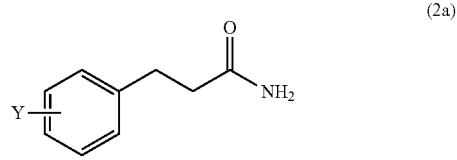

(wherein Y is the same as defined above); or
Step (c): the following Step (a-1) and the following Step (b)

Step (a-1): reacting a compound represented by formula (1)

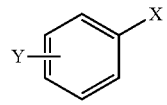
(1)

(wherein X represents a chlorine atom; and Y represents a 4-trifluoromethyl group)

with a compound represented by formula (5b)

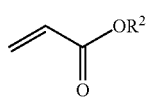
(5b)

(wherein $R^2$ represents a methyl group or an ethyl group)

in the presence of a nickel compound and zinc to produce a compound represented by formula (2b)

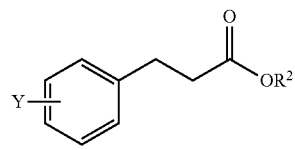
(2b)

(wherein Y and $R^2$ are the same as defined above); and

Step (b): reacting the compound represented by formula (2b) with formamide in the presence of a strong base to produce a compound represented by formula (2a)

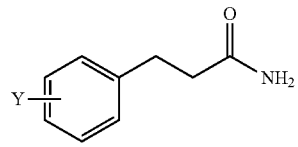
(2a)

(wherein Y is the same as defined above);
and comprising the following Step (d);

Step (d): subjecting the compound represented by formula (2a) to a Hofmann rearrangement to produce a compound represented by formula (3a)

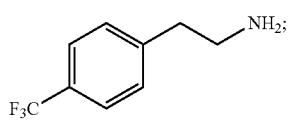
(3a)

and further comprising the following Step (e);

Step (e): reacting the compound represented by formula (3a) with a compound represented by formula (7)

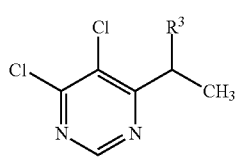
(7)

(wherein $R^3$ is the same as defined above)
to produce the compound represented by formula (8).

8. N-carbomethoxy-2-[4-(trifluoromethyl)phenyl]ethyl-amine.

* * * * *